US012606516B2

(12) United States Patent
Moon et al.

(10) Patent No.: US 12,606,516 B2
(45) Date of Patent: Apr. 21, 2026

(54) METHOD FOR PRODUCING DIESTER-BASED MATERIAL

(71) Applicant: LG CHEM, LTD., Seoul (KR)

(72) Inventors: Jeong Ju Moon, Daejeon (KR); Hyun Kyu Kim, Daejeon (KR); Joo Ho Kim, Daejeon (KR); Yun Ki Cho, Daejeon (KR); Seok Ho Jeong, Daejeon (KR); Woo Hyuk Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 820 days.

(21) Appl. No.: 17/615,787

(22) PCT Filed: Sep. 24, 2020

(86) PCT No.: PCT/KR2020/012937
§ 371 (c)(1),
(2) Date: Dec. 1, 2021

(87) PCT Pub. No.: WO2021/060861
PCT Pub. Date: Apr. 1, 2021

(65) Prior Publication Data
US 2022/0242814 A1 Aug. 4, 2022

(30) Foreign Application Priority Data
Sep. 27, 2019 (KR) ......................... 10-2019-0119987

(51) Int. Cl.
*C07C 67/08* (2006.01)

(52) U.S. Cl.
CPC .................................... *C07C 67/08* (2013.01)

(58) Field of Classification Search
CPC ..... C07C 2601/14; C07C 67/08; C07C 69/40; C07C 69/44; C07C 69/75; C07C 69/80; C07C 69/82
See application file for complete search history.

(56) References Cited

U.S. PATENT DOCUMENTS

| | | | |
|---|---|---|---|
| 5,349,075 A | 9/1994 | van den Berg et al. | |
| 5,532,405 A | 7/1996 | Lyford, IV | |
| 2002/0082443 A1 | 6/2002 | Uemura et al. | |
| 2005/0176986 A1* | 8/2005 | Matsumoto | C08G 63/85 |
| | | | 502/103 |
| 2010/0137631 A1 | 6/2010 | De Munck et al. | |
| 2011/0301377 A1 | 12/2011 | Peters et al. | |
| 2013/0137802 A1 | 5/2013 | Sawada et al. | |
| 2014/0148612 A1 | 5/2014 | DeMunck et al. | |
| 2016/0264509 A1 | 9/2016 | Kaller et al. | |
| 2016/0272780 A1 | 9/2016 | Kim et al. | |
| 2016/0376219 A1 | 12/2016 | Kim et al. | |
| 2019/0263745 A1 | 8/2019 | Lee et al. | |
| 2021/0040026 A1 | 2/2021 | Lee et al. | |

FOREIGN PATENT DOCUMENTS

| | | | |
|---|---|---|---|
| CN | 101631761 A | 1/2010 | |
| CN | 102256922 A | 11/2011 | |
| CN | 101591242 B | 1/2013 | |
| CN | 102958898 A | 3/2013 | |
| CN | 103664621 A | 3/2014 | |
| CN | 104262158 A | 1/2015 | |
| CN | 108329206 A | 7/2018 | |
| ES | 297905 | * | 6/1964 |
| JP | H10-130673 A | 5/1998 | |
| JP | H11-130724 A | 5/1999 | |
| JP | 2002-155026 A | 5/2002 | |
| JP | 2002-193885 A | 7/2002 | |
| JP | 2012-092074 A | 5/2012 | |
| JP | 2016-536313 A | 11/2016 | |
| JP | 2017-509592 A | 4/2017 | |
| JP | 2019-059888 A | 4/2019 | |
| KR | 10-1995-0001683 B1 | 2/1995 | |
| KR | 10-2009-0130042 A | 12/2009 | |
| KR | 10-2013-0101017 A | 9/2013 | |
| KR | 10-2014-0026677 A | 3/2014 | |
| KR | 10-1663586 B1 | 10/2016 | |
| KR | 10-2019-0027622 A | 3/2019 | |
| KR | 10-2019-0027623 A | 3/2019 | |
| RU | 2114819 C1 | 7/1998 | |

(Continued)

OTHER PUBLICATIONS

ES 297905 translation (Year: 1964).*
Rahman et al., "The plasticizer market: an assessment of traditional plasticizers and research trends to meet new challenges" Progress in Polymer Science (2004) vol. 29, pp. 1223-1248.

(Continued)

*Primary Examiner* — Andrew D Kosar
*Assistant Examiner* — Blaine G Doletski
(74) *Attorney, Agent, or Firm* — Bryan Cave Leighton Paisner LLP

(57) ABSTRACT

A method of preparing a raw material mixture by mixing a dicarboxylic acid and a C4-10 mono-alcohol, and obtaining a product mixture including a diester-based material and water by reacting the raw material mixture in the presence of a catalyst. In the first step, at least one among a reactor temperature (Condition A), an alcohol input amount (Condition B), and an inert gas input amount (Condition C) is controlled, and the distinction between a beginning stage of a reaction and an ending stage of the reaction in Conditions A to C above is based on a reaction control point. The reaction control point is a point of time selected at which a conversion rate of the reaction is between 10% and 80%. This method produces a diester-based material with improved reactivity and improved energy expenditure.

7 Claims, No Drawings

(56)  References Cited

FOREIGN PATENT DOCUMENTS

| WO | 95/29888 A1 | 11/1995 |
| WO | 2008/110306 A1 | 9/2008 |
| WO | 2016/043616 A1 | 3/2016 |

OTHER PUBLICATIONS

Janjua et al., "Systemic Uptake of Diethyl Phthalate, Dibutyl Phthalate, and Butyl Paraben Following Whole-body Topical Application and Reproductive and Thyroid Hormone Levels in Humans", Environmental Science and Technology (2007) vol. 41, pp. 5564-5570.

* cited by examiner

METHOD FOR PRODUCING DIESTER-BASED MATERIAL

CROSS-REFERENCE TO RELATED APPLICATIONS

This application is a U.S. national stage of international Application No. PCT/KR2020/012937, filed on Sep. 24, 2020, and claims the benefit of Korean Patent Application No. 10-2019-0119987, filed on Sep. 27, 2019, in the Korean Intellectual Property Office, the disclosures of which are incorporated herein in their entirety by reference.

TECHNICAL FIELD

The present invention relates to a method for producing a diester-based material, the method achieving improved reactivity and productivity.

BACKGROUND ART

Phthalate-based plasticizers occupied 92% of the world's plasticizer market by the 20th century (Mustafizur Rahman and Christopher S. Brazel "The plasticizer market: an assessment of traditional plasticizers and research trends to meet new challenges" Progress in Polymer Science 2004, 29, 1223-1248). Phthalate-plasticizers are additives used to improve the processability of polyvinyl chloride (hereinafter, referred to as PVC) by imparting flexibility, durability, cold resistance, and the like, and lowering viscosity during melting. Phthalate-based plasticizers are introduced into PVC in various amounts and are used not only for hard products such as rigid pipes, but also for soft products such as food packaging materials, blood bags, and flooring materials because the phthalate-based plasticizers are soft and stretchable. Thus, the phthalate-based plasticizers are more closely related to real life than any other materials and are widely used for materials which come into direct contact with a human body.

However, despite the compatibility with PVC and excellent softness imparting properties of phthalate-based plasticizers, there has been controversy over the harmful nature of the phthalate-based plasticizers in that when a PVC product containing a phthalate-based plasticizer is used in real life, the phthalate-based plasticizer may leak from the product at a slow rate and act as a suspected endocrine disruptor (environmental hormone) and a carcinogen, similar to the deleterious effects observed for heavy metals (NR Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2008, 42, 7522-7527). Particularly, a report was published in the 1960s in the United States that discussed the leakage of diethylhexyl phthalate (di-(2-ethylhexyl) phthalate, DEHP), the most commonly used phthalate plasticizer, from PVC products, which resulted in global environmental regulations being implemented in addition to various studies on the harmful nature of the phthalate-based plasticizer on human bodies, boosted by increasing interest in environmental hormones in the 1990s.

Thus, in an effort to respond to environmental hormonal problems and environmental regulations due to the leakage of phthalate-based plasticizers, di(2-ethylhexyl) phthalate in particular, many researchers have been conducting research to develop a new non-phthalate-based plasticizer alternative that does not include phthalic anhydride in the manufacturing of di(2-ethylhexyl) phthalate, to develop a phthalate-based plasticizer which may replace di(2-ethylhexyl) phthalate and be used for industrial purposes because the leakage of the plasticizer is suppressed even though it is a phthalate-based plasticizer, and to develop a leakage suppression technology which suppresses the leakage of phthalate-based plasticizers, thereby significantly reducing risks to human bodies and which meets environmental standards.

As such, the development of materials which are free from environmental problems and which may replace a di(2-ethylhexyl) phthalate having existing environmental problems, such as ester-based plasticizers, is actively underway. In addition, research on developing an ester-based plasticizer with excellent physical properties as well as research on equipment for manufacturing the plasticizer have been actively conducted, and there has been a demand for more efficient, more economical and simpler process designs.

Meanwhile, at most industrial sites, a batch process is used to produce the above-described ester-based plasticizer. In batch processing, a gas-liquid separation system for the reflux of non-reactants and efficient removal of sub-reactants in a reactor (Korean Patent Laid-Open Publication No. 10-2019-0027622) and a system integrating facilities of a primary direct esterification reaction and a second trans-esterification reaction to simplify the batch process (Korean Patent Laid-Open Publication No. 10-2019-0027623) have been introduced.

However, a batch process introduced in the above-described inventions to improve a reaction through the simplification of facilities or change of facilities requires high costs for adding facilities or changing lines in the process, so that it is difficult to apply these methods in the industry. Therefore, there is a demand for the development of a process which is capable of optimizing a reaction through the modification and control of processing conditions.

SUMMARY

An exemplary aspect of the present invention is a method for producing a diester-based material. The method improves a reaction rate by controlling reaction conditions, thereby improving productivity, and which reduces an energy expenditure, thereby improving a process efficiency in producing a diester-based material.

An exemplary aspect of the present invention is a production method including preparing a raw material mixture by mixing a dicarboxylic acid and a C4-10 mono-alcohol (Step S1), and obtaining a product mixture including a diester-based material and water by reacting the raw material mixture in the presence of a catalyst (Step S2). In Step S2, at least one among Conditions A to C, described below, is applied, and the distinction between a beginning stage of a reaction and an ending stage of the reaction in Conditions A to C is based on a reaction control point, which is a point of time at which a conversion rate of the reaction is between 10% and 80%.

The Conditions A to C are as follows:

Condition A: The temperature of a reactor in the beginning stage of the reaction is set to 150° C. to 220° C., and the temperature of the reactor in the ending stage of the reaction is set to 180° C. to 250° C., wherein the temperature of the ending stage is higher than the temperature of the beginning stage;

Condition B: 40 wt % to 90 wt % of a mono alcohol is added in the beginning stage of the reaction, and 10 wt % to 60 wt % of the mono alcohol is added in the ending stage of the reaction based on the total input amount of the mono alcohol; and Condition C: 10 vol % to 50 vol % of an inert gas is added in the beginning stage of the reaction, and 50 vol % to 90 vol % of the inert gas is added in the ending stage of the reaction based on the total input amount of an inert gas.

According to the present invention, there may be provided a method for producing a diester-based material, the method having a fast reaction rate and thus capable of improving productivity, and having an improved energy expenditure and thus capable of reducing processing costs, and having high efficiency.

DETAILED DESCRIPTION

Hereinafter, the present invention will be described in more detail to facilitate understanding of the present invention. It will be understood that words or terms used in the specification and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor may properly define the meaning of the words or terms to best explain the invention.

The term "composition" as used herein includes not only a reaction product and a decomposition product formed from materials of a corresponding composition, but also a mixture of materials including the corresponding composition.

The term "straight vinyl chloride polymer" as used herein may mean, as one of the types of vinyl chloride polymers, one which has been polymerized through suspension polymerization, bulk polymerization, or the like, and which is in the shape of porous particles in which a large amount of pores having a size of tens to hundreds of micrometers are distributed, and has no cohesiveness but has excellent flowability.

The term "paste vinyl chloride polymer" as used herein may mean, as one of the types of vinyl chloride polymers, one polymerized through micro-suspension polymerization, micro-seed polymerization, emulsion polymerization, or the like, and refers to a polymer which are particles with no fine and dense pores having a size of tens to thousands of nanometers, and has cohesiveness but has poor flowability.

The prefix "iso-" as used herein generally means that a methyl branch is coupled to an end of an alkyl group. However, unless otherwise defined and named herein, in the present specification, the prefix means an alkyl group in which a methyl group or an ethyl group is coupled as a branched chain to a main chain of the alkyl group, and is used to encompass an alkyl group in which a methyl group or ethyl group is coupled as a branched chain to the main chain of the alkyl group as well as being coupled to the end of the alkyl group. The prefix also includes the meaning of a mixture of such alkyl groups.

The terms 'including' and 'having,' and derivatives thereof, whether they are specifically disclosed or not, do not intend to exclude the presence of any additional components, steps or procedures. In order to avoid any uncertainty, all compositions claimed through the use of the term 'including' may include any additional additives, supplements, or compounds, whether they are polymers or others, unless otherwise stated. In contrast, the term 'consisting essentially of' excludes any other components, steps, or procedures from the scope of any subsequent description, except that it is not essential to operability. The term 'consisting of' excludes any components, steps or procedures which are not specifically stated or listed.

Method for Producing Diester-Based Material

According to an exemplary embodiment of the present invention, there is provided a production method including preparing a raw material mixture by mixing a dicarboxylic acid and a C4-10 mono-alcohol (Step S1), and obtaining a product mixture including a diester-based material and water, which are produced by reacting the raw material mixture in the presence of a catalyst (Step S2), wherein in Step S2, at least one among Conditions A to C below is applied, and the distinction between a beginning stage of a reaction and an ending stage of the reaction is based on a reaction control point, which is a point of time at which a conversion rate of the reaction is between 10% and 80%.

The Conditions A to C are as follows:

Condition A: The temperature of a reactor in the beginning stage of the reaction is set to 150° C. to 220° C., and the temperature of the reactor in the ending stage of the reaction is set to 180° C. to 250° C., wherein the temperature of the ending stage is higher than the temperature of the beginning stage, Condition B: 40 wt % to 90 wt % of the mono alcohol is added in the beginning stage of the reaction, and 10 wt % to 60 wt % of the mono alcohol is added in the end stage of the reaction, based on the total input amount of the mono alcohol, and Condition C: 10 vol % to 50 vol % of the inert gas is added in the beginning stage of the reaction, and 50 vol % to 90 vol % is added in the ending stage of the reaction, based on the total input amount of an inert gas.

Raw Material Mixture Preparation Step (S1)

The production method according to an exemplary embodiment of the present invention starts with preparing a raw material mixture, and the raw material mixture includes a dicarboxylic acid and a C4-10 mono-alcohol. In some cases, one type of each of the dicarboxylic acid and mono alcohol may be used, but a mixture of two or more types thereof may also be used.

It is preferable that raw materials of the raw material mixture are not individually introduced into a reactor in which a reaction is performed but are introduced into the reactor in the state of being as uniformly mixed as possible through mixing before being introduced into the reactor, introduction of a dicarboxylic acid and a mono-alcohol individually into a reactor as raw materials is not excluded. However, when the dicarboxylic acid and the mono-alcohol are pre-mixed and then introduced in the form of a raw material mixture with sufficient preheating through utilizing waste heat, the reaction may be easily performed. Additionally, in general, a reaction catalyst is separated from the raw material mixture to be introduced into a reactor. In this case, the reaction catalyst is pre-heated and then brought into contact with the raw material mixture, so that it is possible to prevent a side reaction from occurring when the raw material mixture is heated with the catalyst from the beginning.

The dicarboxylic acid included in the raw material mixture may include, for example, one or more selected from the group consisting of an isophthalic acid, a terephthalic acid, a succinic acid, an adipic acid, a cyclohexane 1,2-dicarboxylic acid, a cyclohexane 1,3-dicarboxylic acid, and a cyclohexane 1,4-dicarboxylic acid.

In addition, the mono-alcohol may be C4 to C10, preferably C5 to C9, and more preferably C6 to C9. For example, the mono-alcohol may include one or more selected from the group consisting of n-butanol, isobutanol, n-pentanol, iso-pentanol, n-hexanol, isohexanol, n-heptanol, isoheptanol, n-octanol, 2-ethylhexanol, n-nonanol, isononanol, decanol, isodecanol, and 2-propylheptanol. A mixture of two or more alcohols may be used, and a diester-based material may be produced as a composition using a mixture of structural isomers of the alcohol.

Esterification Reaction Step (S2)

In the production method according to an exemplary embodiment of the present invention, after the raw material mixture is prepared, a step of subjecting the raw material mixture to an esterification reaction under specific conditions to obtain a diester-based material and product water is performed.

The esterification reaction may be, more specifically, performed by adding a catalyst to the raw material mixture, which is a mixture of the dicarboxylic acid and the mono-alcohol, and reacting them under a nitrogen atmosphere.

According to an exemplary embodiment of the present invention, in the esterification reaction, a specific point of time is determined as a reaction control point, and based on the reaction control point, a beginning stage of the reaction and an ending stage of the reaction are distinguished and Conditions A to C are applied accordingly. The reaction control point is selected to be a time at which a reaction conversion rate is between 10% and 80%, and the lower limit range of the conversion rate which may be selected as the reaction control point may be preferably 15%, more preferably 20%, and even more preferably 25%, and the upper limit range thereof may be preferably 75%, more preferably 70%, and even more preferably 60%. When a point of time at which the conversion rate is less than 10% is selected as the reaction control point, the energy expenditure may increase while the improvement in reaction rate is not great. When a point of time at which the reaction progresses past a point of time at which the conversion rate is 80% is selected as the reaction control point, it becomes a factor which rather worsens the reaction rate, so that the meaning of changing the reaction condition may fade away.

That is, to implement both an improvement in reaction rate and an improvement in energy expenditure, it may be desirable that a reaction control point within the above range is selected. The beginning stage of the reaction may mean a conversion rate before a reaction control point is passed, and the ending stage of the reaction may mean a conversion rate after the reaction control point has passed.

According to an exemplary embodiment of the present invention, Conditions A to C are as follows.

Condition A: The temperature of a reactor in the beginning stage of the reaction is set to 150° C. to 220° C., and the temperature of the reactor in the ending stage of the reaction is set to 180° C. to 250° C., Condition B: 40 wt % to 90 wt % of the mono alcohol is added in the beginning stage of the reaction, and 10 wt % to 60 wt % of the mono alcohol is added in the ending stage of the reaction based on the total input amount of the mono alcohol, and Condition C: 10 vol % to 50 vol % of the inert gas is added in the beginning stage of the reaction, and 50 vol % to 90 vol % of the inert gas is added in the ending stage of the reaction based on the total input amount of an inert gas.

Conditions A to C above are conditions to be applied after the reaction raw material is introduced and the catalyst is introduced. Condition A is used to set the temperature of the reactor and Conditions B and C are used to control the input amounts of the mono-alcohol and the inert gas, respectively.

Meanwhile, the production method is performed in a reactor, and the reactor may have a configuration of a reaction unit including a stripper connected to an upper portion of the reactor and performing gas-liquid separation on an unreacted mono-alcohol, which is a material to be vaporized, and product water, and a condenser and a decanter to condense and separate a gas discharged from the stripper. The reaction of Step S2 may be performed in such a reaction unit.

Specifically, when the raw material mixture of the dicarboxylic acid and the mono-alcohol is introduced to the reactor to begin the reaction, a reaction temperature is higher than the boiling point of the mono-alcohol, so that water (product water) is generated as a reaction by-product together with a diester-based material, causing vaporization. The esterification reaction is an equilibrium reaction, and the product water, which is a reaction by-product, is continuously removed, and the vaporized unreacted mono-alcohol is sent back to the reactor to smoothly perform the reaction. Therefore, a mixed gas of the product water and the unreacted mono-alcohol is separated through the stripper, the condenser, and the decanter to recirculate the mono-alcohol back to the reactor and to discharge the product water out of a system or to utilize the same as process water in a process.

Hereinafter, which condition should be controlled in which manner in such a reaction environment so as to be effective in terms of energy expenditure improvement and reaction rate improvement will be described.

Control of Reaction Temperature

According to an exemplary embodiment of the present invention, Condition A among the conditions to be controlled relates to changing the set temperature of a reactor. At the beginning of a reaction, the reaction is performed by setting the temperature of the reactor within the range of 150° C. to 220° C., and then when a reaction control point is passed, the set temperature of the reactor is changed to a temperature of 180° C. to 250° C. In this case, the temperature of the reactor in the ending stage of the reaction is set to be higher than the temperature of the reactor in the beginning stage of the reaction.

The set temperature of the reactor is not necessarily the same as the temperature of reactants therein. Even when the temperature of the reactor is set to 200° C., the reactants may be in the process of being heated to 200° C., may have already been heated to the same temperature, or may be at a lower temperature.

When the initial temperature of the reactor is set to be between 150° C. and 220° C., the initial reflux of mono-alcohol may be suppressed and unnecessary heat loss may be prevented. When the initial temperature of the reactor is set to a temperature lower than 150° C., the reaction rate is too low, thereby increasing the side reaction rate with a catalyst. When the initial temperature of the reactor is set to a temperature higher than 220° C., there may be unnecessary heat loss and reactants may be thermally damaged, and it may be impossible to improve the reaction rate due to the surge in the reflux amount of alcohol. Therefore, it may be necessary to set the initial temperature of the reactor at an appropriate level.

When the reaction control point has passed, the reaction has been already performed to a certain level, and thus, the temperature should be increased to an appropriate level to maximize the reaction conversion rate. In this case, it is necessary to set the temperature to a value between 180° and 250° C. If the temperature is set to a temperature lower than 180° C., the conversion rate may not reach up to 99%, and the purity of a product may not be achieved to a desired level. If the temperature is set to a temperature higher than 250° C., reactants are more likely to be thermally damaged and there is a high possibility of scale generation on the inner wall of the reactor due to the reactant, product, or catalyst. Furthermore, due to an increase in the reflux amount in the ending stage of the reaction, it may take a long time for the conversion rate to exceed 99%, or it may not be possible to achieve the conversion rate of 99%.

Accordingly, as described above, when the temperature of the reactor is set according to the control condition, it may be effective in terms of preventing the above-described limitations in advance and improving the energy expenditure if the temperature of the reactor in the beginning stage of the reaction is set to a temperature selected from 150° C. to 220° C., and the temperature of the reactor in the ending stage of the reaction is changed to a value from 180° C. to 250° C. Preferably, the temperature of the reactor in the beginning stage of the reaction may be set to 160° C. to 190° C., and the temperature of the reactor in the ending stage of the reaction may be set to 200° C. to 250° C.

Control of Alcohol Input Amount Condition

According to an exemplary embodiment of the present invention, Condition B among the conditions to be controlled divides the input amounts of an alcohol. The amount of the alcohol to be introduced into a reactor or to a mixer in the beginning stage of a reaction is 40% to 90 wt % based on the total input amount of alcohol, and in the ending stage of the reaction after the reaction control point has passed, the remainder 10% to 60 wt %, which is obtained by subtracting the amount introduced in the beginning stage of the reaction from the total input amount, is introduced. At this time, based on the reaction control point, the alcohol may be introduced in batches at the start of the reaction, continuously introduced throughout the entire reaction, or divided within the range of input amount of the beginning stage of the reaction and introduced. In the ending stage of the reaction, the same method may be applied, and the introduction method may be independently applied in the beginning and ending stages of the reaction.

In general, the alcohol may be used in the range of 150 mol % to 500 mol %, 200 mol % to 400 mol %, 200 mol % to 350 mol %, 250 mol % to 400 mol %, or 270 mol % to 330 mol % based on 100 mol % of dicarboxylic acid. When the input amount selected from the above range is set to 100 wt %, 40 wt % to 90 wt % may be introduced in the beginning stage of the reaction and the remainder may be introduced in the ending stage of the reaction.

If a mono-alcohol is introduced in an amount less than 40 wt % based on the total input amount in the beginning stage of the reaction, the energy expenditure may increase with no improvement in reaction rate. That means an amount greater than 60 wt % is introduced in the ending stage of the reaction, and the input amount of alcohol to be additionally introduced to a reactant which has already heated is greater than 60 wt %. Therefore, a phenomenon which suppresses the reaction based on the generation of reaction heat may occur. In addition, since a forward reaction is not the primary reaction, and water is not removed due to an increase in the amount of mono-alcohol in the azeotrope with the remaining water, a situation in which the catalyst is deactivated or a situation in which the reverse reaction becomes the primary reaction may occur. As a result, the reaction rate may decrease and the energy expenditure may increase.

In addition, when the mono-alcohol is introduce in an amount greater than 90 wt % in the beginning stage of the reaction, the energy expenditure may rapidly increase. If there is a large amount of mono-alcohol present in the reactor, the reaction rate is expected to be high due to the dominant effect of the forward reaction. However, the reaction rate may decrease due to the increase in initial alcohol reflux, and there may be a problem in which energy loss caused by the increase in reflux amount is increased.

Accordingly, when the input amount of mono-alcohol is selected as a control condition, setting the amount of alcohol to be introduced in the beginning stage of the reaction to 40 wt % to 90 wt % based on the total input amount of alcohol and setting the amount of alcohol to be introduced in the ending stage of the reaction to 10 wt % to 60 wt %, which is the remainder of the total amount of alcohol, may be effective in reducing the energy expenditure and improving the reaction rate. In addition, when the input amount of alcohol is controlled to be within the above range, the reactivity may be expected to improve contrary to a theoretical prediction because the reaction contact area of the diester-based material and the mono-alcohol is increased compared to when 100% of the input amount of alcohol is introduced from the beginning, which controls the esterification reaction. The amount of alcohol to be introduced in the beginning stage of the reaction may be preferably set to 40 wt % to 80 wt % based on the total input amount of alcohol, and the amount of alcohol to be introduced in the ending stage of the reaction may be preferably set to 20 wt % to 60 wt % based on the total input amount of alcohol. More preferably, the input amount thereof may be set to 40 wt % to 70 wt % in the beginning stage, and may be set to 30 wt % to 60 wt % in the ending stage.

Control of Inert Gas Input Amount Condition

According to an exemplary embodiment of the present invention, Condition C controls the divided input amounts of inert gas. The inert gas introduced into a reactor in the beginning stage of a reaction is 10 vol % to 50 vol % based on the total input amount of inert gas, and the inert gas introduced in the ending stage of the reaction, that is, after a reaction control point, is the remainder 50 vol % to 90 vol %, which is obtained by subtracting the input amount of the beginning stage from the total input amount. At this time, based on the reaction control point, the inert gas may be introduced in batches into a reactor filled with reactants at the start of the reaction, continuously introduced throughout the entire reaction, or divided within the range of input amount of the beginning stage of the reaction and introduced. In the ending stage of the reaction, the same method may be applied, and the introduction method may be independently applied in the beginning and ending stages of the reaction.

The inert gas may be one or more selected from the group consisting of nitrogen, argon, and helium, and serves to control a reflux amount to discharge product water. If the total amount of inert gas is introduced from the beginning, or the inert gas exceeding 50 vol % of the total input amount is introduced before the reaction control point is reached, there may be a problem of energy expenditure due to the increase in the reflux amount. If the input amount of the inert gas is less than 10 vol %, it is difficult to discharge the product water, which may cause a problem of reaction delay. Therefore, when the input amount of inert gas is controlled to be within the above range, reactivity and productivity may be improved. Preferably, 10 vol % to 40 vol % of the inert gas may be introduced based on the total input amount of inert gas in the beginning stage of the reaction, and 60 vol % to 90 vol % of the inert gas may be introduced in the ending stage of the reaction.

According to an exemplary embodiment of the present invention, in Step S2 of the production method, at least one among Conditions A to C is applied. The problems observed when all of Conditions A to C are not applied may be partially offset by applying at least one of Conditions A to C. For example, when Condition A is applied, the problem when Conditions B and C are not applied may be partially offset, and the same may apply when Condition B is applied but the remainder does not apply, or when Condition C is applied but the remainder does not apply.

When the aforementioned reactor temperature (Condition A), input amount of mono-alcohol (Condition B), and input amount of inert gas (Condition C) are controlled in combination with each other or independently based on a specific conversion rate, even when any one thereof is applied, a remarkable effect in improving reactivity compared to the prior art may be expected. When the reaction is divided into a beginning stage and an ending stage based on a specific conversion rate, and two or more, or all of the above conditions are applied thereto in combination, a diester-based material may be produced at optimum efficiency.

That is, in terms of improving the energy expenditure and improving the reaction rate, two or more of Conditions A to C may be preferably applied, and more preferably, Conditions A and B may be applied, and most preferably, all of Conditions A to C may be applied.

The production method according to an exemplary embodiment of the present invention controls reaction conditions such as the aforementioned temperature of a reactor, input amount and time at which the mono-alcohol is input, and input amount and time at which the inert gas is input based on the conversion rate of a reaction, thereby improving reactivity and productivity through designing optimum reaction conditions. Accordingly, the amount of energy expenditure, the purity of a product, or the reaction time may reach an excellent level.

When reaction conditions are controlled in combination as described above, effects of controlling a reflux amount in consideration of energy expenditure, improving reactivity through the improvement of reaction rate and temperature raising rate, and improving product quality through the smooth discharge of generated product water may all be optimized and achieved.

Meanwhile, the catalyst may be one or more selected from an acid catalyst such as sulfuric acid, hydrochloric acid, phosphoric acid, nitric acid, paratoluenesulfonic acid, methanesulfonic acid, ethanesulfonic acid, propanesulfonic acid, butanesulfonic acid, and alkyl sulfuric acid, a metal salt such as aluminum lactate, lithium fluoride, potassium chloride, cesium chloride, calcium chloride, iron chloride, and phosphoric acid, a metal oxide such as heteropoly acid, a natural/synthetic zeolite, a cation and anion exchange resin, and an organic metal such as tetraalkyl titanate and a polymer thereof, and may preferably be tetraalkyl titanate. As a specific example, the catalyst may be tetraalkyl titanate.

The amount of a catalyst to be used may vary depending on the type thereof. In one example, a homogeneous catalyst may be used in an amount of 0.01 wt % to 5 wt %, 0.01 wt % to 3 wt %, 1 wt % to 5 wt %, or 2 wt % to 4 wt % based on 100 wt % of reactants, and a heterogeneous catalyst may be used in an amount of 5 wt % to 200 wt %, 5 wt % to 100 wt %, 20 wt % to 200 wt %, or 20 wt % to 150 wt % based on the total weight of the reactants.

Product Mixture Neutralization Step (S3)

According to an exemplary embodiment of the present invention, the production method may further include neutralizing the product mixture obtained in Step S2 by adding a neutralizer containing an alkali metal hydroxide and water.

As the alkali metal hydroxide used in the neutralization, sodium hydroxide or potassium hydroxide may be used, and the sodium hydroxide or the potassium hydroxide may be dissolved in water at a concentration of 0.1% to 10% and applied as an aqueous solution. The neutralization step may be a process of deactivating the catalyst remaining in the product mixture by introducing the above aqueous alkali metal hydroxide solution. At this time, a salt is generated and removed as a solid product, and the product mixture may be separated into an organic layer containing a diester-based material and an aqueous layer containing water, and these layers may be discharged separately.

The product mixture subjected to the above neutralization step is discharged as an organic layer containing a diester-based material. At this time, the discharged organic layer may undergo a predetermined purification process to produce a diester-based material, and the water layer may be go through a wastewater treatment system to recover the mono-alcohol and recycle the water as process water.

Plasticizer Composition and Resin Composition

According to another exemplary embodiment of the present invention, a plasticizer composition including the diester-based material produced by the production method described above is provided.

The plasticizer composition may include components commonly used, and is not particularly limited thereto.

The plasticizer composition may include an epoxidized alkyl ester composition, and a plasticizer composition including the epoxidized alkyl ester composition may be used alone, and a mixed plasticizer further containing a secondary plasticizer may also be used.

As the secondary plasticizer, a terephthalate-based material, an isophthalate-based material, a phthalate-based material, a cyclohexane 1,4-diester-based material, a cyclohexane 1,2-diester-based material, a cyclohexane 1,3-diester-based material, a trimellitate-based material, a citrate-based material, an epoxidized oil, a succinate-based material, a benzoate-based material, a glycol-based material, and a mixture thereof may be used.

Specifically, the materials listed above as a secondary plasticizer are all materials having an ester group, and as an alkyl group coupled to the ester group, an n-butyl group, an isobutyl group, an n-pentyl group, an isopentyl group, an n-hexyl group, an isohexyl group, an n-heptyl group, an isoheptyl group, a 2-ethylhexyl group, an octyl group, an n-nonyl group, an isononyl group, a 2-propylheptyl group, a decyl group, an isodecyl group, and the like may be used.

According to yet another exemplary aspect of the present invention, a resin composition including the plasticizer composition and a resin is provided.

As the resin, a resin commonly known in the art may be used. For example, a mixture of one or more selected from the group consisting of a straight vinyl chloride polymer, a paste vinyl chloride polymer, an ethylene vinyl acetate copolymer, an ethylene polymer, a propylene polymer, polyketone, polystyrene, polyurethane, natural rubber, synthetic rubber, and a thermoplastic elastomer, and the like may be used as the resin. However, the present invention is not limited thereto.

The plasticizer composition may be included in an amount of 5 parts to 150 parts by weight, preferably 5 parts to 130 parts by weight, or 10 parts to 120 parts by weight based on 100 parts by weight of the resin.

In general, a resin in which a plasticizer composition is used may be manufactured as a resin product through melt processing or plastisol processing, and a melt processed resin and a plastisol processed resin may be produced differently depending on each polymerization method.

For example, when the vinyl chloride polymer is used for melt processing, solid resin particles produced by suspension polymerization and the like, thereby having a large average particle diameter are used, and such vinyl chloride polymer is referred to as a straight vinyl chloride polymer. When used for plastisol processing, a sol-like resin having fine resin particles produced by emulsion polymerization, and the like is used, and such vinyl chloride polymer is referred to as a paste vinyl chloride resin.

At this time, in the case of the straight vinyl chloride polymer, a plasticizer is preferably included in the range of 5 parts to 80 parts by weight based on 100 parts by weight of the polymer, and in the case of the paste vinyl chloride polymer, a plasticizer is preferably included in the range of 40 parts to 120 parts by weight based on 100 parts by weight of the polymer.

The resin composition may further include a filler. The filler may be included in an amount of 0 parts to 300 parts by weight based on 100 parts by weight of the resin, preferably 50 parts to 200 parts by weight, and more preferably 100 parts to 200 parts by weight.

The filler may be a filler known in the art, and is not particularly limited. For example, the filler may be a mixture of one or more selected from silica, magnesium carbonate, calcium carbonate, hard coal, talc, magnesium hydroxide, titanium dioxide, magnesium oxide, calcium hydroxide, aluminum hydroxide, aluminum silicate, magnesium silicate, and barium sulfate.

In addition, the resin composition may further include other additives such as a stabilizer, if necessary. Other additives such as the stabilizer may be included in an amount of 0 to 20 parts by weight based on 100 parts by weight of the resin, preferably 1 part to 15 parts by weight.

The stabilizer may be, for example, a calcium-zinc-based (Ca—Zn-based) stabilizer such as a complex stearic acid salt of calcium-zinc, or a barium-zinc-based (Ba—Zn based) stabilizer, but is not particularly limited thereto.

As described above, the resin composition may be applied to both melting processing and plastisol processing. For example, calendering processing, extrusion processing, or injection processing may be used as the melting processing, and coating processing or the like may be used as the plastisol processing.

EXAMPLES

Hereinafter, the present invention will be described in detail with reference to various exemplary embodiments. However, the exemplary embodiments according to the present invention can be modified into various different forms, and the scope of the present invention should not be construed as being limited to the exemplary embodiments described below. The exemplary embodiments of the present invention are provided to more fully describe the present invention to those skilled in the art.

(1) Application of Condition A

Examples, Reference Example, and Comparative Examples 498 g of isophthalic acid as a dicarboxylic acid and 1172 g of 2-ethylhexanol as a mono-alcohol were pre-mixed, and then the mixture was introduced to a 3.0 L reactor. Thereafter, tetrabutyl titanate was introduced thereto as a catalyst to proceed with a reaction. Reaction conditions of each of Examples, Reference Example, and Comparative Examples are as described in Table 1 below.

TABLE 1

| | Reaction temperature (° C.) | | Alcohol input | Inert gas input | |
| --- | --- | --- | --- | --- | --- |
| | In the beginning | In the end | amount (wt %) | amount (vol %) | Conversion rate (%) |
| Example 1-1 | 160 | 250 | 100 | 100 | 10 |
| Example 1-2 | 180 | 220 | 100 | 100 | 20 |
| Example 1-3 | 200 | 220 | 100 | 100 | 20 |
| Example 1-4 | 200 | 220 | 100 | 100 | 80 |
| Reference Example | 220 | 220 | 100 | 100 | — |
| Comparative Example 1-1 | 230 | 250 | 100 | 100 | 80 |
| Comparative Example 1-2 | 230 | 250 | 100 | 100 | 10 |
| Comparative Example 1-3 | 140 | 220 | 100 | 100 | 10 |
| Comparative Example 1-4 | 140 | 220 | 100 | 100 | 80 |

Experimental Example 1

The degree of energy improvement and the degree of reactivity improvement with respect to Examples, Reference Example, and Comparative Examples were indexed according to the following measurement criteria, and the results are shown in Table 2 below.

1) Energy improvement index: Based on the energy consumption of Reference Example, which was set to 0, steps were divided from −5 to 10, with −3 having large energy expenditure and steps closer to 10 having smaller energy expenditure, thereby representing greater improvement. The energy expenditure is the sum of energy consumed to introduce an alcohol refluxed to an upper portion of a reactor back into the reactor and energy consumed to apply reaction heat. The reflux amount of alcohol was evaluated by measuring the flow rate of a column disposed at the upper portion of the reactor and performing gas-liquid separation on the refluxed alcohol, and the reaction heat was measured by the amount of steam required to set the temperature of the reactor.

2) Reactivity improvement index: Based on the reactivity of Reference Example, which was set to 5, steps were divided from 1 to 10, with steps closer to 1 representing reactivity lower than that of Reference Example (wherein, the reaction rate was low and it took a long time to achieve a conversion rate of 99%) and steps closer 10 representing excellent reactivity (wherein, the reaction rate is high, and it took a long time to achieve a conversion rate of 99%). The evaluation was made based on the reaction time required to achieve a conversion rate of 99%.

TABLE 2

| | Energy improvement index | Reactivity improvement Index |
| --- | --- | --- |
| Example 1-1 | 5 | 4 |
| Example 1-2 | 7 | 5 |
| Example 1-3 | 5 | 5 |
| Example 1-4 | 4 | 6 |
| Reference Example | 0 | 5 |
| Comparative Example 1-1 | −3 | 5 |
| Comparative Example 1-2 | −5 | 4 |

TABLE 2-continued

| | Energy improvement index | Reactivity improvement Index |
|---|---|---|
| Comparative Example 1-3 | 0 | 2 |
| Comparative Example 1-4 | — | — |

Referring to Table 2 above, in the case of Examples 1-1 to 1-4 in which the temperature of the reactor in the beginning stage of the reaction and the ending stage of the reaction was set to be within the range of the present invention and then the temperature was raised, it can be confirmed that energy improvement and reactivity improvement were excellent. On the other hand, in the case of Comparative Example 1-1 in which the temperature of the reactor in the beginning stage of the reaction was set too high and then the temperature was maintained until the conversion rate reached 80%, it was confirmed that the degree of energy improvement became worse compared to that of Reference Example in which the reaction was performed without changing the temperature. In the case of Comparative Example 1-2 in which the temperature of the reactor was changed when the conversion rate was 10%, since the initial temperature of the reactor was too high, the energy expenditure became even worse, and the reactivity also became worse. Furthermore, in the case of Comparative Example 1-3 in which the temperature of the reactor in the beginning stage of the reaction was set too low, it was confirmed that the initial reactivity of the reaction was poor. When the low temperature of the reactor was maintained until the conversion rate reached 80% and then the temperature was changed, the reaction did not occur until the conversion rate reached 99%, it was not possible to measure energy improvement and reactivity improvement.

As a result, it can be seen that when the reaction is performed by setting the temperature of the reactor in the beginning stage of the reaction and in the ending stage of the reaction to be within the range of the present invention and then raising the temperature, it is possible to simultaneously achieve both energy improvement and reactivity improvement.

(2) Application of Condition B

Examples, Reference Example, and Comparative Examples 498 g of isophthalic acid as a dicarboxylic acid and 1172 g (the total amount introduced in the beginning and ending stages) of 2-ethylhexanol as a mono-alcohol were pre-mixed, and then the mixture was introduced to a 3.0 L reactor. Thereafter, tetrabutyl titanate was introduced thereto as a catalyst to proceed with a reaction. Reaction conditions of each of Examples, Reference Example, and Comparative Examples are as described in Table 3 below.

TABLE 3

| | Reaction temperature (° C.) | Alcohol input amount (wt %) | | Inert gas input amount (vol %) | Con-version rate (%) |
|---|---|---|---|---|---|
| | | In the beginning | In the end | | |
| Example 2-1 | 220 | 40 | 60 | 100 | 10 |
| Example 2-2 | 220 | 70 | 30 | 100 | 55 |
| Example 2-3 | 220 | 90 | 10 | 100 | 55 |
| Example 2-4 | 220 | 90 | 10 | 100 | 80 |

TABLE 3-continued

| | Reaction temperature (° C.) | Alcohol input amount (wt %) | | Inert gas input amount (vol %) | Con-version rate (%) |
|---|---|---|---|---|---|
| | | In the beginning | In the end | | |
| Example 2-5 | 220 | 70 | 30 | 100 | 10 |
| Example 2-6 | 220 | 70 | 30 | 100 | 80 |
| Reference Example | 220 | 100 | — | 100 | — |
| Comparative Example 2-1 | 220 | 95 | 5 | 100 | 80 |
| Comparative Example 2-2 | 220 | 95 | 5 | 100 | 10 |
| Comparative Example 2-3 | 220 | 20 | 80 | 100 | 10 |
| Comparative Example 2-4 | 220 | 20 | 80 | 100 | 80 |
| Comparative Example 2-5 | 220 | 70 | 30 | 100 | 5 |
| Comparative Example 2-6 | 220 | 70 | 30 | 100 | 90 |

Experimental Example 2

The degree of energy improvement and the degree of reactivity improvement with respect to Examples, Reference Example, and Comparative Examples were measured and indexed by the same standards and methods as in Experimental Example 1, and the results are shown in Table 4 below.

TABLE 4

| | Energy improvement index | Reactivity improvement index |
|---|---|---|
| Example 2-1 | 8 | 7 |
| Example 2-2 | 8 | 8 |
| Example 2-3 | 2 | 7 |
| Example 2-4 | 3 | 6 |
| Example 2-5 | 4 | 6 |
| Example 2-6 | 9 | 7 |
| Reference Example | 0 | 5 |
| Comparative Example 2-1 | 2 | 5 |
| Comparative Example 2-2 | 1 | 5 |
| Comparative Example 2-3 | 3 | 3 |
| Comparative Example 2-4 | — | — |
| Comparative Example 2-5 | 1 | 6 |
| Comparative Example 2-6 | 3 | 3 |

Referring to Table 4 above, in the case of Examples 2-1 to 2-6 in which the total input amount of alcohol input was divided into appropriate amounts and introduced in the beginning stage and the ending stage of the reaction, it was confirmed that the degree of energy improvement and reactivity improvement was very excellent. On the other hand, in the case of Comparative Examples 2-1 and 2-2, the alcohol was introduced in an excess amount at the beginning, so that the degree of energy improvement and the degree of reactivity improvement were very insignificant. It was confirmed that the result was the same even if the timing of divided input was changed. In the case of Comparative Example 2-3, the alcohol was introduced in a very small amount at the beginning, so that it was confirmed that the reactivity became rather worse and the degree of energy improvement was insignificant. In the case of Comparative Example 2-4 in which the timing of divided input was changed to when the conversion rate was 80%, the reaction did not occur, so that it was not possible to take the measurement. In addition, when comparing Example 2-5 and Comparative Example 2-5, although there was only a 5% difference in the conversion rate, it has been confirmed that there were three stages of difference in the degree of energy improvement. When comparing Example 2-6 and Comparative Example 2-6, although the conditions were all the same except that a conversion rate of 90% was applied instead of a conversion rate of 80%, it was confirmed that the degree of energy improvement and the degree of reactivity improvement were extremely different between Example 2-6 and Comparative Example 2-6.

As a result, it can be confirmed that energy improvement and reactivity improvement may be simultaneously achieved when the alcohol is divided into appropriate amounts and introduced in the beginning stage and the ending stage of the reaction.

(3) Application of Condition C

Examples, Reference Example, and Comparative Examples 498 g of isophthalic acid as a dicarboxylic acid and 1172 g of 2-ethylhexanol as a mono-alcohol were pre-mixed, and then the mixture was introduced to a 3.0 L reactor. Thereafter, tetrabutyl titanate was introduced thereto as a catalyst to proceed with a reaction. Reaction conditions of each of Examples, Reference Example, and Comparative Examples are as described in Table 5 below.

Table 5

| | Reaction temperature (° C.) | Inert gas input amount (vol %) | | Alcohol input amount (wt %) | Conversion rate (%) |
|---|---|---|---|---|---|
| | | In the beginning | In the end | | |
| Example 3-1 | 220 | 10 | 90 | 100 | 50 |
| Example 3-2 | 220 | 30 | 70 | 100 | 50 |
| Example 3-3 | 220 | 40 | 60 | 100 | 50 |
| Reference Example | 220 | 100 | — | 100 | — |
| Comparative Example 3-1 | 220 | 70 | 30 | 100 | 50 |

Example, and Comparative Examples were measured and indexed by the same standards and methods as in Experimental Example 1, and the results are shown in Table 6 below.

TABLE 6

| | Energy improvement index | Reactivity improvement index |
|---|---|---|
| Example 3-1 | 3 | 6 |
| Example 3-2 | 2 | 6 |
| Example 3-3 | 1 | 5 |
| Reference Example | 0 | 5 |
| Comparative Example 3-1 | −2 | 4 |

Referring to Table 6 above, in the case of Examples 3-1 to 3-3 in which the total input amount of inert gas was divided into appropriate amounts and introduced in the beginning stage and the ending stage of the reaction, it was confirmed that the degree of energy improvement and reactivity improvement was relatively excellent. On the other hand, in the case of Comparative Example 3-1, the inert gas was introduced in an excess amount at the beginning, so that both the degree of energy improvement and the degree of reactivity improvement became worse. As a result, it can be confirmed that energy improvement and reactivity improvement may be simultaneously achieved when the inert gas is divided into appropriate amounts and introduced in the beginning stage and the ending stage of the reaction.

(4) Application of Two or More Conditions

Examples, Reference Example, and Comparative Examples 498 g of isophthalic acid as a dicarboxylic acid and 1172 g (the total amount introduced in the beginning and ending stages) of 2-ethylhexanol as a mono-alcohol were pre-mixed, and then the mixture was introduced to a 3.0 L reactor. Thereafter, tetrabutyl titanate was introduced thereto as a catalyst to proceed with a reaction. Reaction conditions of each of Examples, Reference Example, and Comparative Examples are as described in Table 7 below.

TABLE 7

| | Reaction temperature (° C.) | | Alcohol input amount (wt %) | | Inert gas input amount (vol %) | | Conversion rate (%) |
|---|---|---|---|---|---|---|---|
| | In the beginning | In the end | In the beginning | In the end | In the beginning | In the end | |
| Example 4-1 | 220 | 220 | 70 | 30 | 10 | 90 | 10 |
| Example 4-2 | 220 | 220 | 70 | 30 | 10 | 90 | 80 |
| Example 4-3 | 180 | 220 | 100 | — | 10 | 90 | 20 |
| Example 4-4 | 180 | 220 | 70 | 30 | 100 | — | 50 |
| Example 4-5 | 220 | 220 | 70 | 30 | 10 | 90 | 55 |
| Example 4-6 | 180 | 220 | 70 | 30 | 10 | 90 | 50 |
| Reference Example | 220 | 220 | 100 | — | 100 | — | — |
| Comparative Example 4-1 | 180 | 220 | 70 | 30 | 100 | — | 5 |
| Comparative Example 4-2 | 180 | 220 | 70 | 30 | 100 | — | 90 |

Experimental Example 3

The degree of energy improvement and the degree of reactivity improvement with respect to Examples, Reference

Experimental Example 4

The degree of energy improvement and the degree of reactivity improvement with respect to Examples, Reference Example, and Comparative Examples were measured and indexed by the same standards and methods as in Experimental Example 1, and the results are shown in Table 8 below.

TABLE 8

|  | Energy improvement index | Reactivity improvement index |
|---|---|---|
| Example 4-1 | 5 | 6 |
| Example 4-2 | 10 | 7 |
| Example 4-3 | 8 | 6 |
| Example 4-4 | 9 | 8 |
| Example 4-5 | 9 | 8 |
| Example 4-6 | 10 | 10 |
| Reference Example | 0 | 5 |
| Comparative Example 4-1 | 0 | 5 |
| Comparative Example 4-2 | 3 | 1 |

Referring to Table 8 above, in Examples 4-1 to 4-6, two or more among the reaction conditions of A to C were applied, and it can be confirmed that the degree of improvement in energy and reactivity was significantly increased compared to that of Reference Example. On the other hand, in the case of Comparative Examples 4-1 and 4-2, the reaction control point was not properly selected when the above conditions were applied. Accordingly, in the case of Comparative Example 4-1, although the same conditions as in Example 4-4 were applied, the degree of energy improvement was extremely different between Example 4-4 and Comparative Example 4-1, and the degree of reactivity improvement was the same. As a result, it was confirmed that when the reaction control point was not properly set, the result was the same as when the conditions were not applied. In the case of Comparative Example 4-2, the reaction control point was at to be a point of time at which the conversion rate was too high, so that it was confirmed that the reactivity became rather worse and the energy improvement was insignificant. As a result, it is confirmed that it is preferable to apply two or more of Conditions A to C in order to simultaneously achieve energy improvement and reactivity improvement. Furthermore, it is confirmed that the difference in effect is very large depending on the selection of a reaction control point.

The invention claimed is:

1. A production method comprising:
   a step of mixing a dicarboxylic acid and a C4-10 mono-alcohol to prepare a raw material mixture; and
   a step of reacting the raw material mixture in the presence of a catalyst to obtain a product mixture,
   wherein the product mixture comprises a diester-based material and water, wherein Conditions A, B and C are applied during the step of reacting the raw material mixture in the presence of the catalyst, and wherein a beginning stage and an ending stage of a reaction are determined based on a reaction control point, which is a point of time at which a conversion rate of the reaction is in a range of 10% to 80%:

Condition A: a temperature of a reactor in the beginning stage of the reaction is set to 150° C. to 220° C., and the temperature of the reactor in the ending stage of the reaction is set to 180° C. to 250° C., wherein the temperature of the ending stage is higher than the temperature of the beginning stage, Condition B: a portion of the raw material mixture having 40 wt % to 90 wt % of the total amount of the C4-C10 mono-alcohol is added in the beginning stage of the reaction, and a remaining portion of the raw material mixture having 10 wt % to 60 wt % of the C4-C10 mono-alcohol is added in the ending stage of the reaction, Condition C: 10 vol % to 50 vol % of the total amount of inert gas is divided and added in the beginning stage of the reaction, and 50 vol % to 90 vol % of the inert gas is added in the ending stage of the reaction based on the total input amount of the inert gas.

2. The method of claim 1, wherein during the application of Condition A, the temperature of the reactor in the beginning stage of the reaction is set to 160° C. to 190° C. and the temperature of the reactor in the ending stage of the reaction is set to 200° C. to 250° C.

3. The method of claim 1, wherein during the application of Condition B, 40 wt % to 85 wt % of the mono-alcohol is added in the beginning stage of the reaction and 15 wt % to 60 wt % of the mono-alcohol is added in the ending stage of the reaction based on the total amount of the mono alcohol.

4. The method of claim 1, wherein the raw material mixture is pre-heated to a temperature less than or equal to 150° C. in the absence of a catalyst.

5. The method of claim 1, further comprising neutralizing the product mixture by adding an alkali metal hydroxide and water produced during the step of reacting the raw material mixture in the presence of a catalyst.

6. The method of claim 1, wherein the dicarboxylic acid comprises one or more selected from the group consisting of an isophthalic acid, a terephthalic acid, a succinic acid, an adipic acid, a cyclohexane 1,2-dicarboxylic acid, a cyclohexane 1,3-dicarboxylic acid, and a cyclohexane 1,4-dicarboxylic acid.

7. The method of claim 1, wherein the mono-alcohol is a C5 to C9 alcohol.

* * * * *